(12) United States Patent
Glazer et al.

(10) Patent No.: US 11,785,187 B2
(45) Date of Patent: Oct. 10, 2023

(54) MONITORING CAMERA AND MOUNT

(71) Applicant: Udisense Inc., New York, NY (US)

(72) Inventors: Assaf Glazer, Kiryat Ono (IL); Tor Ivry, Rishon Lezion (IL); Amir Katz, Bat Hefer (IL); Amnon Kami, New York, NY (US); Mark Prommel, Brooklyn, NY (US); Pil Ho Chung, Palisades Park, NJ (US); Marco Perry, Brooklyn, NY (US); Oscar Frias, Brooklyn, NY (US); Gal Shkedi, Rinatya (IL)

(73) Assignee: UDISENSE INC., New York, NY (US)

( * ) Notice: Subject to any disclaimer, the term of this patent is extended or adjusted under 35 U.S.C. 154(b) by 0 days.

(21) Appl. No.: 17/676,872

(22) Filed: Feb. 22, 2022

(65) Prior Publication Data
US 2022/0182585 A1 Jun. 9, 2022

Related U.S. Application Data

(63) Continuation of application No. 15/931,601, filed on May 14, 2020, now Pat. No. 11,297,284, which is a
(Continued)

(51) Int. Cl.
*G06V 20/52* (2022.01)
*A61B 5/11* (2006.01)
(Continued)

(52) U.S. Cl.
CPC .......... *H04N 7/183* (2013.01); *A61B 5/1114* (2013.01); *A61B 5/1128* (2013.01);
(Continued)

(58) Field of Classification Search
CPC ...................................... H04N 7/183
See application file for complete search history.

(56) References Cited

U.S. PATENT DOCUMENTS

| | | |
|---|---|---|
| 4,895,162 A | 1/1990 | Dolliver |
| 5,914,660 A | 6/1999 | Mesibov et al. |
| | (Continued) | |

FOREIGN PATENT DOCUMENTS

WO 2013186696 A1 12/2013

OTHER PUBLICATIONS

U.S. Appl. No. 17/092,351 Office Action dated May 10, 2022.
(Continued)

*Primary Examiner* — Irfan Habib
(74) *Attorney, Agent, or Firm* — KLIGLER & ASSOCIATES PATENT ATTORNEYS LTD

(57) ABSTRACT

A video monitoring system includes a camera head, which includes an infrared illumination source and an image sensor and is configured to transmit streaming video signals generated by the image sensor. A mount is configured to hold the camera head in a fixed location and orientation above a bed such that the image sensor captures images from a bird's eye view of a child in the bed. A processor is configured to receive and analyze the video signals so as to extract and provide information to a client device with regard to a behavior of the child.

18 Claims, 12 Drawing Sheets

Related U.S. Application Data continuation of application No. 16/091,989, filed as application No. PCT/US2017/031486 on May 7, 2017, now Pat. No. 10,708,550, which is a continuation-in-part of application No. 15/361,702, filed on Nov. 28, 2016, now Pat. No. 10,165,230, which is a continuation of application No. 14/681,573, filed on Apr. 8, 2015, now Pat. No. 9,530,080.

(60) Provisional application No. 62/333,294, filed on May 9, 2016, provisional application No. 62/333,227, filed on May 8, 2016, provisional application No. 61/976,666, filed on Apr. 8, 2014.

(51) Int. Cl.

| | |
|---|---|
| A61B 5/00 | (2006.01) |
| H04N 5/33 | (2023.01) |
| G06F 18/21 | (2023.01) |
| H04N 7/18 | (2006.01) |
| G06V 40/20 | (2022.01) |
| G06V 10/147 | (2022.01) |
| H04N 23/50 | (2023.01) |
| H04N 23/51 | (2023.01) |
| H04N 23/56 | (2023.01) |
| H04N 23/661 | (2023.01) |

(52) U.S. Cl.
CPC .......... *A61B 5/4809* (2013.01); *A61B 5/4815* (2013.01); *A61B 5/6891* (2013.01); *G06F 18/217* (2023.01); *G06V 10/147* (2022.01); *G06V 20/52* (2022.01); *G06V 40/20* (2022.01); *H04N 5/33* (2013.01); *H04N 23/50* (2023.01); *H04N 23/51* (2023.01); *H04N 23/56* (2023.01); *H04N 23/661* (2023.01); *A61B 2503/04* (2013.01)

(56) References Cited

U.S. PATENT DOCUMENTS

| | | | | |
|---|---|---|---|---|
| 6,113,455 | A * | 9/2000 | Whelan | A63H 33/006 248/214 |
| 6,687,523 | B1 | 2/2004 | Jayaramen et al. | |
| 6,991,384 | B1 * | 1/2006 | Davis | F16M 11/041 396/428 |
| 7,277,122 | B2 * | 10/2007 | Sakai | H04N 21/6587 348/E5.042 |
| 7,318,051 | B2 * | 1/2008 | Weston | G06F 18/2113 706/12 |
| 7,397,380 | B1 * | 7/2008 | Smolsky | G08B 21/0453 340/573.7 |
| 7,470,167 | B2 * | 12/2008 | Clark | H04N 7/18 446/175 |
| 7,624,074 | B2 * | 11/2009 | Weston | G06N 20/00 706/1 |
| 7,774,032 | B2 * | 8/2010 | Swan | G08B 21/0476 455/127.5 |
| 7,827,631 | B2 * | 11/2010 | Holman | A47D 7/03 5/100 |
| 8,461,996 | B2 * | 6/2013 | Gallagher | A61B 5/113 600/595 |
| 8,484,774 | B2 * | 7/2013 | Cohen | A47D 9/012 5/93.1 |
| 8,640,280 | B2 * | 2/2014 | Gutierrez | A47D 7/03 5/100 |
| 8,646,126 | B2 * | 2/2014 | Carta | A47D 7/03 5/100 |
| 8,878,679 | B2 | 11/2014 | Arndt et al. | |
| 8,922,653 | B1 * | 12/2014 | Reeve | H04N 7/181 348/143 |
| 8,953,674 | B2 * | 2/2015 | Henson | H04N 7/188 375/240.09 |
| 9,075,290 | B1 * | 7/2015 | Thieman | F16M 13/022 |
| 9,268,465 | B1 * | 2/2016 | Yari | G06Q 50/01 |
| 9,301,710 | B2 | 4/2016 | Mestha et al. | |
| 9,330,343 | B2 * | 5/2016 | Nakano | G06F 18/217 |
| 10,004,278 | B2 | 6/2018 | O'Donnell | |
| 10,874,332 | B2 * | 12/2020 | Glazer | G08B 21/0208 |
| 2003/0057749 | A1 * | 3/2003 | Buono | B60R 11/04 297/217.3 |
| 2003/0233806 | A1 * | 12/2003 | Kuebler | E04H 12/12 362/431 |
| 2007/0076935 | A1 | 4/2007 | Jeung et al. | |
| 2007/0177792 | A1 * | 8/2007 | Ma | G06V 40/25 382/155 |
| 2008/0016624 | A1 * | 1/2008 | Osborn | A63H 33/006 5/658 |
| 2008/0309765 | A1 * | 12/2008 | Dayan | H04N 7/185 348/158 |
| 2009/0066671 | A1 * | 3/2009 | Kweon | G06F 3/0421 345/175 |
| 2010/0060448 | A1 * | 3/2010 | Larsen | A63H 33/006 340/539.15 |
| 2011/0044533 | A1 * | 2/2011 | Cobb | G06V 20/52 348/143 |
| 2011/0129210 | A1 * | 6/2011 | McGucken | G03B 17/561 705/26.5 |
| 2011/0310247 | A1 * | 12/2011 | Rensin | H04L 67/148 709/219 |
| 2011/0313325 | A1 * | 12/2011 | Cuddihy | G08B 21/0476 600/595 |
| 2012/0062735 | A1 * | 3/2012 | Rivera | G08B 21/0476 348/143 |
| 2012/0083670 | A1 | 4/2012 | Rotondo et al. | |
| 2012/0243747 | A1 | 9/2012 | Kielkopf et al. | |
| 2013/0035599 | A1 | 2/2013 | De Bruijn et al. | |
| 2013/0169735 | A1 * | 7/2013 | Barker | G08B 21/0208 348/14.02 |
| 2013/0241730 | A1 * | 9/2013 | Saitwal | G08B 29/185 340/540 |
| 2013/0324876 | A1 | 12/2013 | Bernal et al. | |
| 2013/0342691 | A1 * | 12/2013 | Lewis | H04N 7/18 348/143 |
| 2013/0342693 | A1 * | 12/2013 | Lee | H04N 7/18 348/143 |
| 2014/0072206 | A1 * | 3/2014 | Eaton | G06N 3/006 382/159 |
| 2014/0121540 | A1 * | 5/2014 | Raskin | G16H 40/63 600/479 |
| 2014/0142435 | A1 | 5/2014 | Bernal et al. | |
| 2014/0334058 | A1 * | 11/2014 | Galvan | F41G 1/35 361/232 |
| 2015/0109441 | A1 * | 4/2015 | Fujioka | H04N 7/183 348/143 |
| 2015/0302717 | A1 | 10/2015 | Denittis et al. | |
| 2016/0015278 | A1 * | 1/2016 | Campo | G06V 20/52 348/143 |
| 2016/0183695 | A1 * | 6/2016 | Veron | G08B 25/08 5/93.1 |
| 2016/0255341 | A1 | 9/2016 | Mateti et al. | |
| 2016/0310067 | A1 * | 10/2016 | Heinrich | H04N 7/183 |
| 2017/0221226 | A1 | 8/2017 | Shen et al. | |
| 2017/0319114 | A1 * | 11/2017 | Kaestle | A61B 5/7278 |
| 2018/0014736 | A1 | 1/2018 | Misharin | |
| 2019/0122390 | A1 | 4/2019 | Schneider et al. | |
| 2019/0205655 | A1 * | 7/2019 | Matsuoka | G06V 20/52 |

OTHER PUBLICATIONS

CN Application # 2018800747622 Office Action dated Aug. 11, 2022.
U.S. Appl. No. 17/092,351 Office Action dated Aug. 23, 2022.
EP Application # 18882218.3 Summons to attent Oral Proceedings dated Oct. 17, 2022.

(56) References Cited

OTHER PUBLICATIONS

CN Application # 2018800747622 Office Action dated Jan. 19, 2023.

* cited by examiner

MONITORING CAMERA AND MOUNT

CROSS-REFERENCE TO RELATED APPLICATION

This application is a continuation of U.S. patent application Ser. No. 15/931,601, filed May 14, 2020, which is a continuation of U.S. patent application Ser. No. 16/091,989, filed Oct. 7, 2018 (now U.S. Pat. No. 10,708,550), in the national phase of PCT Patent Application PCT/US2017/031486, filed May 7, 2017, which claims the benefit of U.S. Provisional Patent Application 62/333,227, filed May 8, 2016, and of U.S. Provisional Patent Application 62/333,294, filed May 9, 2016. PCT/US2017/031486 is a continuation in part of U.S. patent application Ser. No. 15/361,702, filed Nov. 28, 2016 (now U.S. Pat. No. 10,165,230), which is a continuation of U.S. patent application Ser. No. 14/681,573, filed Apr. 8, 2015 (now U.S. Pat. No. 9,530,080), which claims the benefit of U.S. Provisional Patent Application 61/976,666, filed Apr. 8, 2014. All of these related applications are incorporated herein by reference.

FIELD OF THE INVENTION

The present invention relates generally to sleep monitoring, and particularly to apparatus, systems and methods for video-based monitoring of a sleeping infant.

BACKGROUND

Video-based sleep monitors for infants are known in the art. For example, U.S. Pat. No. 8,922,653 describes a crib mobile and surveillance system which communicates video data captured by a camera within a mobile member housing, and sounds received by a microphone disposed in a base, to a handheld monitor. The video data are displayed and broadcast in real time on a monitor screen on the handheld monitor to remotely monitor a child lain in a crib having the present device.

As another example, U.S. Patent Application Publication 2013/0342693 describes a video-enabled baby monitoring system including a transmitter with a camera feature, which captures motion and includes microprocessors that generate a series of video signal codes, which are transmitted at specific radio frequencies to a dedicated receiver unit. The transmitter unit also includes an infrared light source and a sound capture source, wherein the sound capture source generates sound signal codes. Another unit provides for enhanced, convenient data transfer from the transmitter unit and may be selected from a number of adaptor docking stations; or a smart phone platform; or a docking cradle with Wi-Fi capability.

SUMMARY

Embodiments of the present invention that are described hereinbelow provide devices, systems and methods for monitoring an infant in a crib.

There is therefore provided, in accordance with an embodiment of the invention, a video monitoring system, including a camera head, which includes an infrared illumination source and an image sensor. A mount is configured to hold the camera head in a fixed location and orientation above a crib, so that the image sensor captures images of the crib and an intervention region adjacent to the crib from a fixed perspective.

In the disclosed embodiments, the mount is selected from a set of mounts including a base having multiple legs for floor mounting and a flat base for at least one of shelf mounting and wall mounting, and the camera head is configured to be attached to and detached from any of the mounts in the set. In one embodiment, the camera head includes a receptacle configured to accept a plug on the mount, and the plug on each of the mounts has a distinguishing feature that fits into the receptacle and enables the camera head to identify the mount to which the camera head is attached.

In one embodiment, the mount includes a tripod base including three legs, wherein one of the legs is rotatable or removable in order to transform the mount from a freestanding configuration to a wall-supported configuration. Additionally or alternatively, the mount is configured to stand between the crib and a wall adjacent to the crib and includes at least one overmolded set screw, which is configured both to enable rotation and locking of the mount and to serve as a bumper against the wall.

Typically, the infrared illumination source directs infrared illumination toward the crib from a lower side of the camera head. In a disclosed embodiment, the camera head includes a night light, which is configured to emit visible illumination from an upper side of the camera head.

In some embodiments, the camera head is configured to transmit streaming video signals generated by the image sensor. In a disclosed embodiment, the camera head is configured to transmit the streaming video signals over a local network in data packets that are addressed so that the video signals are forwarded both to a local client device on the local network and via a public network to a remote server, from which video images are available to a remote client device.

Additionally or alternatively, the system includes a server, wherein the camera head is configured to transmit the streaming video signals over the network to the server, and the server is configured to analyze the video signals so as to extract and provide behavioral information regarding sleep patterns of an infant in the crib. Typically, the server is further configured to analyze the video signals so as to detect actions taken by a caregiver in the intervention region.

There is also provided, in accordance with an embodiment of the invention, sleep monitoring apparatus, including a memory, which is configured to receive and store a stream of images captured by a camera mounted over a crib in which an infant is put to sleep. A processor is configured to analyze the stream of the images so as to detect and log events associated with sleep behavior of the infant.

In some embodiments, the images include an intervention region adjacent to the crib, and at least some of the events that are detected and logged by the processor are based on analyzing actions of a caregiver in the intervention region. Typically, the processor is configured to classify the images according to states, selected from a set of states including an infant awake state, an infant asleep state, an infant away from crib state, and a caregiver visiting state. In a disclosed embodiment, the processor is configured to classify a sequence of the images in which changes are identified in the intervention region as belonging to the caregiver visiting state. Additionally or alternatively, the processor is configured to output messages to a client device responsively to events including predefined transitions among the states. Further additionally or alternatively, the processor is configured to classify the images in the caregiver visiting state into sub-states including a check-in sub-state, a taking care sub-state, an infant removal sub-state and an infant placement sub-state.

Further additionally or alternatively, the processor is configured to output a summary of the logged events to a client device. In a disclosed embodiment, the processor is configured to present the summary in a graphical form, which indicates states of the sleep behavior of the infant and visits by a caregiver and respective periods of time during which the states occurred. In another embodiment, the summary includes video clips associated with the logged events for display on the client device. In a further embodiment, the processor is configured to evaluate a quality of sleep of the infant, based on the logged events.

There is additionally provided, in accordance with an embodiment of the invention, a method for monitoring, which includes providing a camera head, including an infrared illumination source and an image sensor for mounting in a fixed location and orientation above a crib. An image captured by the camera head is displayed, while overlaying on the image a graphical element corresponding to desired boundaries of the crib in a location in the image chosen so that when an actual boundary of the crib in the image is aligned with the graphical element, the image sensor captures images of the crib and an intervention region adjacent to the crib from a fixed perspective.

There is further provided, in accordance with an embodiment of the invention, a method for sleep monitoring, which includes receiving a stream of images captured by a camera mounted over a crib in which an infant is put to sleep. The stream of the images is analyzed so as to detect and log events associated with sleep behavior of the infant.

The present invention will be more fully understood from the following detailed description of the embodiments thereof, taken together with the drawings in which:

DETAILED DESCRIPTION OF EMBODIMENTS

Overview

The above-mentioned U.S. Pat. No. 9,530,080 describes a system for monitoring a baby, comprising a camera head configured at a predefined working point above a baby crib to obtain visual output signals. A network interface controller transfers the visual output signals to client devices and to an analysis server. The analysis server performs computer vision and machine learning analysis on the visual output signals, compares the computer vision and machine learning analysis to comparative data, correlates the computer vision and machine learning analysis to events based on the comparison, and transmits messages based on the events correlating to the computer vision and machine learning analysis to the client devices.

Some embodiments of the present invention that are described hereinbelow provide camera heads of this sort, along with camera mounts and ancillary devices, with enhanced ease of use, versatility, reliability and safety. The camera head is designed and configured to have a bird's eye view from a fixed, well-defined location above the crib (i.e., a location that does not change over long periods, although the precise choice of location can differ from one installation to another) in order to enable efficient and reliable processing of the images captured by the camera head. The camera head can be attached to and detached from a number of different mounting solutions (in addition to the crib mount described in the above-mentioned patent application), including freestanding, wall-mounted, and shelf-mounted versions. In all cases, the camera head is oriented in a fixed position above the crib and out of reach of the child. The camera head is designed to be portable to the degree that it can be attached to a travel base that can be easily carried and placed on a suitable dresser or shelf, for example. The electronic components are contained inside the camera shell, which facilitates simple attachment to different bases and mounting solutions.

In other embodiments that are described herein, an analysis server analyzes video and other data in order to extract and provide behavioral information associated with infant sleep patterns, along with caregiver interactions with the infant. This information can be presented, inter alia, as part of a downloadable application ("app"), which runs on a client device, such as the smartphone of a parent or other caregiver, and receives data from the analysis server, as well as a video stream from the monitoring camera itself. The server thus assists caregivers not only in observing the present state of the infant, but also in understanding and modifying behavioral patterns in a way that can improve the infant's sleeping habits.

System Description

Figure 1:
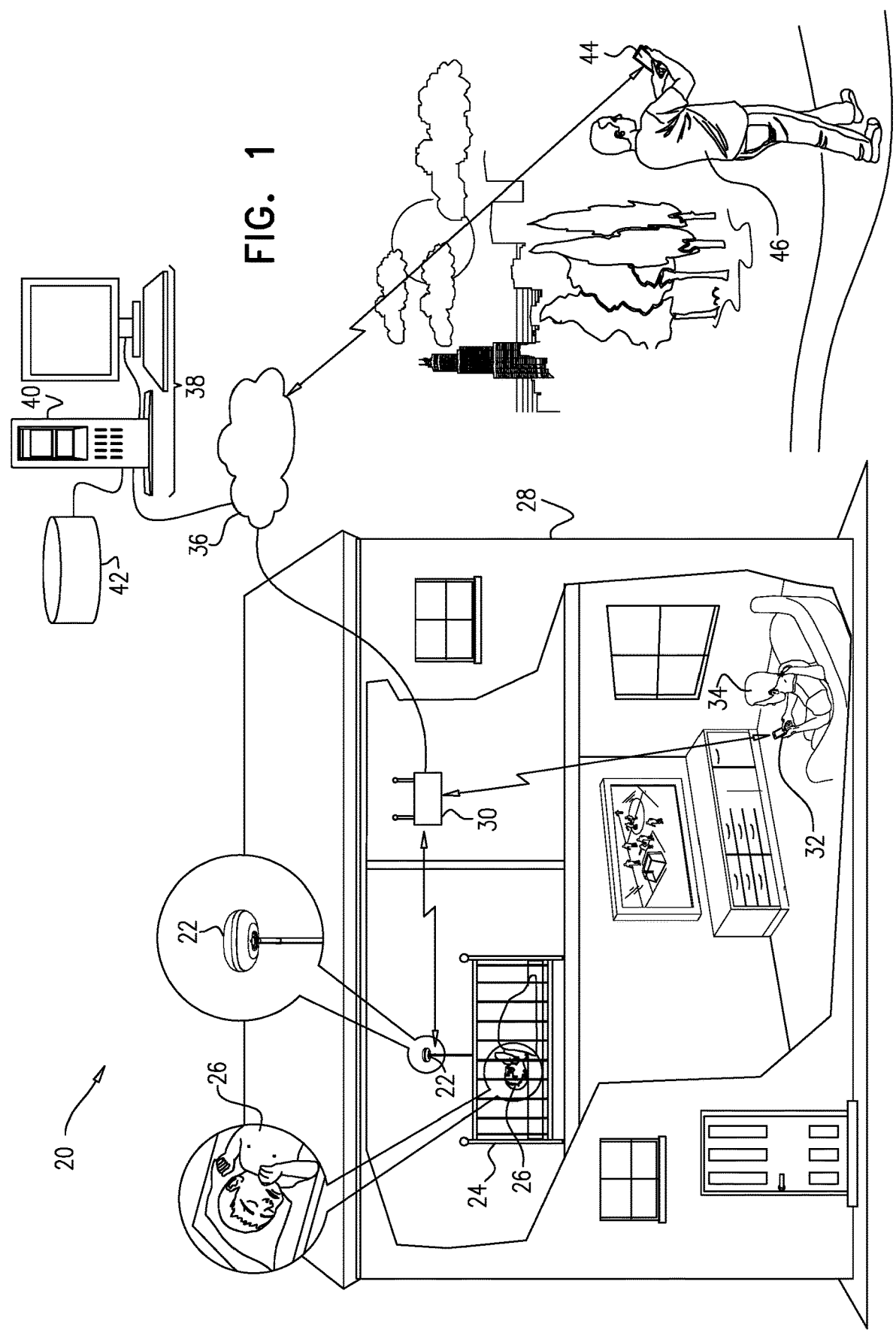
FIG. 1 is a block diagram that schematically illustrates a system for infant sleep monitoring, in accordance with an embodiment of the invention.

FIG. 1 is a block diagram that schematically illustrates a system 20 for infant sleep monitoring, in accordance with an embodiment of the invention. A monitoring camera head 22 is mounted in a fixed location and orientation above a crib 24, in which an infant 26 is sleeping in a residence 28. Camera head 22 transmits digitized streaming video, and possibly other signals, as well, over a local network to a router 30, typically via a wireless local area network (LAN) link, such as a Wi-Fi connection, or a wired link, such as an Ethernet connection.

Camera head 22 transmits the digitized video data in packets that are addressed so that router 30 forwards the video packets both to a local client device 32 on the local network and via a public network 36, such as the Internet, to a remote server 38. Client device 32 typically comprises a smart phone, tablet or personal computer, which enables a caregiver 34 in another room of residence 28 to monitor infant 26, even when there is no Internet connection available. Server 38 makes video images available to authorized remote client devices 44, thus enabling a caregiver 46 to monitor infant 26 at any location where there is access to public network 36. The Wi-Fi or other local network connection provides reliable video streaming from camera head 22 to client device 32 with high bandwidth and low latency, even if the external Internet connection is not working. As long as the Internet is connected, however, the video stream is also transmitted to server 38 for purposes of analysis and retransmission.

Server 38 typically comprises a general-purpose computer, comprising a processor 40 and a memory 42, which receives, stores and analyzes images from camera head 22 in residence 28 and similarly from other cameras in other residences (not shown). Processor 40 analyzes the images and provides caregivers 34 and 46 with reports regarding the infant's sleeping patterns, as well as evaluations and suggestions to assist the caregivers in improving the infant's sleep habits. Some examples of these reporting and evaluation functions are described hereinbelow. Processor 40 typically performs these functions under the control of software, which may be downloaded to server 38 in electronic form, over a network, for example, as well as stored on tangible, non-transitory computer-readable media, such as magnetic, optical or electronic memory media. Alternatively or additionally, some of the processing and monitoring functions may be performed locally, for example by a microprocessor in camera head 22. Further alternatively or additionally, camera head 22 may transmit only a portion of the video data to server 38, such as video segments in which infant 26 is moving.

Figure 2B:
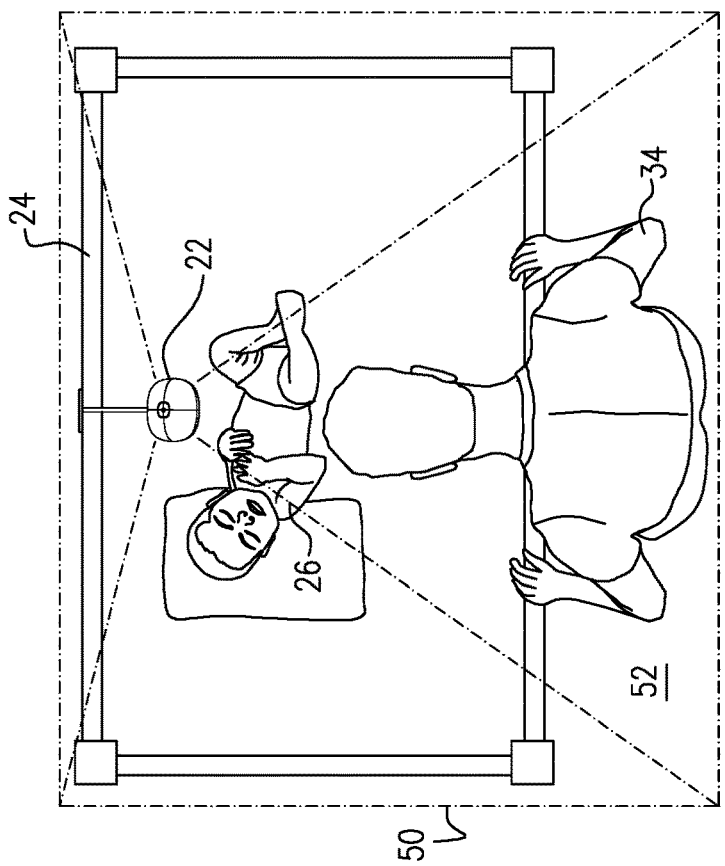
FIG. 2B is a schematic top view of the sleep monitoring device and crib of FIG. 2A.
Figure 2A:
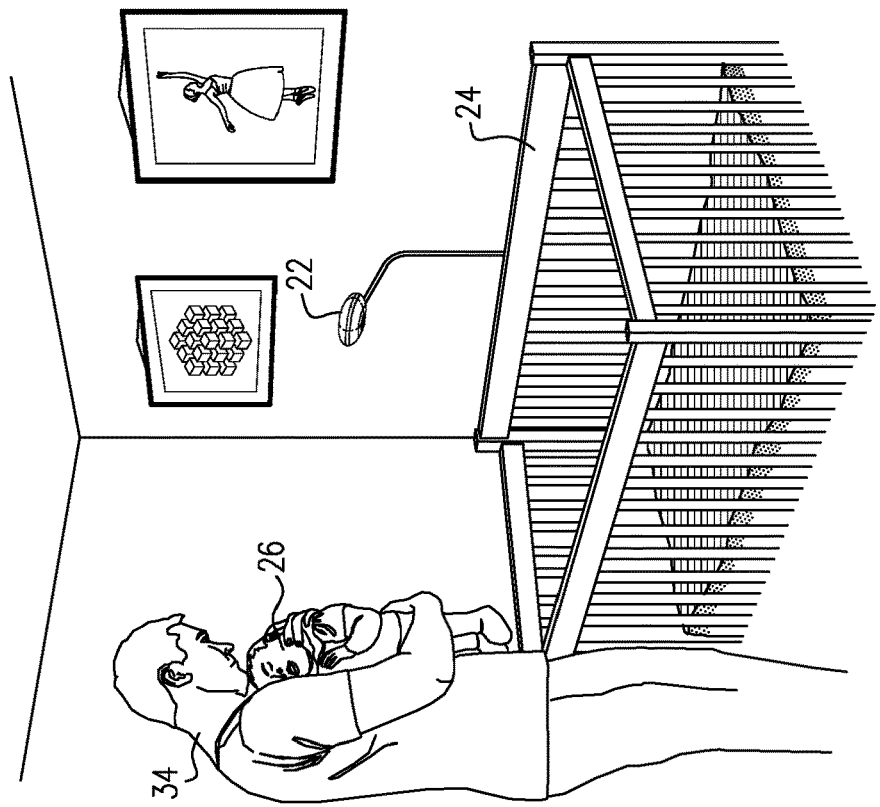
FIG. 2A is a schematic pictorial illustration of a sleep monitoring device mounted over an infant's crib, in accordance with an embodiment of the invention.

FIGS. 2A and 2B schematically show details of the deployment and use of monitoring camera head 22 over crib 24, in accordance with an embodiment of the invention. FIG. 2A is a pictorial illustration, while FIG. 2B is a top view. In this embodiment, monitoring camera head 22 stands against a wall over crib 24. The wall-standing configuration is recommended when the crib is placed against the wall for two reasons: The user can push the crib all the way against the wall; and two bumpers on the vertical part of the mount (shown in FIG. 9) add extra friction that make it harder for a child to rock the mount from side to side. In both the wall-standing and free-standing configurations, the mount cannot fall into the crib, and at worst will fall on the floor outside the crib. In addition, the mount can be fixed to the wall for additional security.

Figure 7:
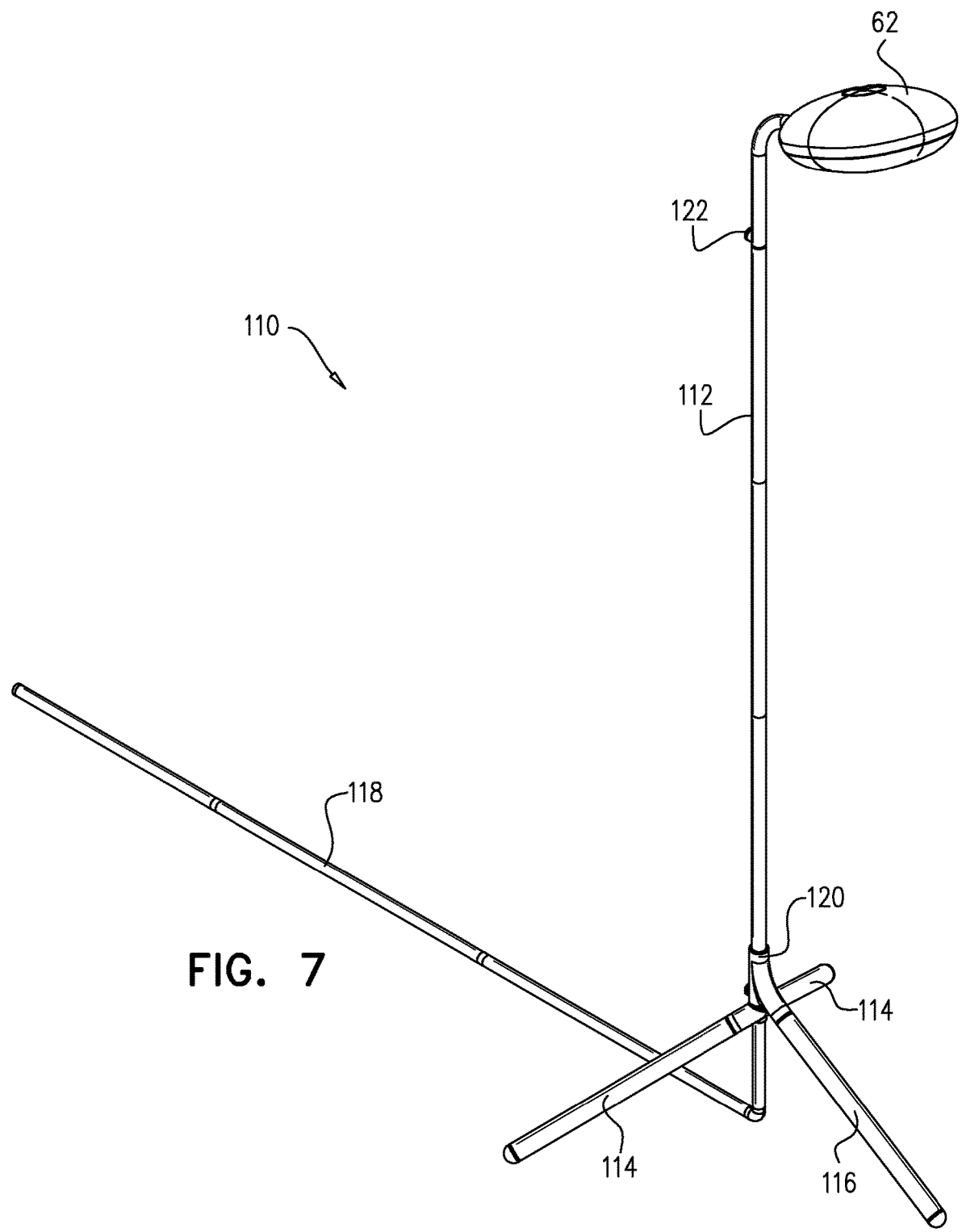
FIG. 7 is a schematic pictorial view of a freestanding sleep monitoring device, in accordance with an embodiment of the invention.
Figure 8A:
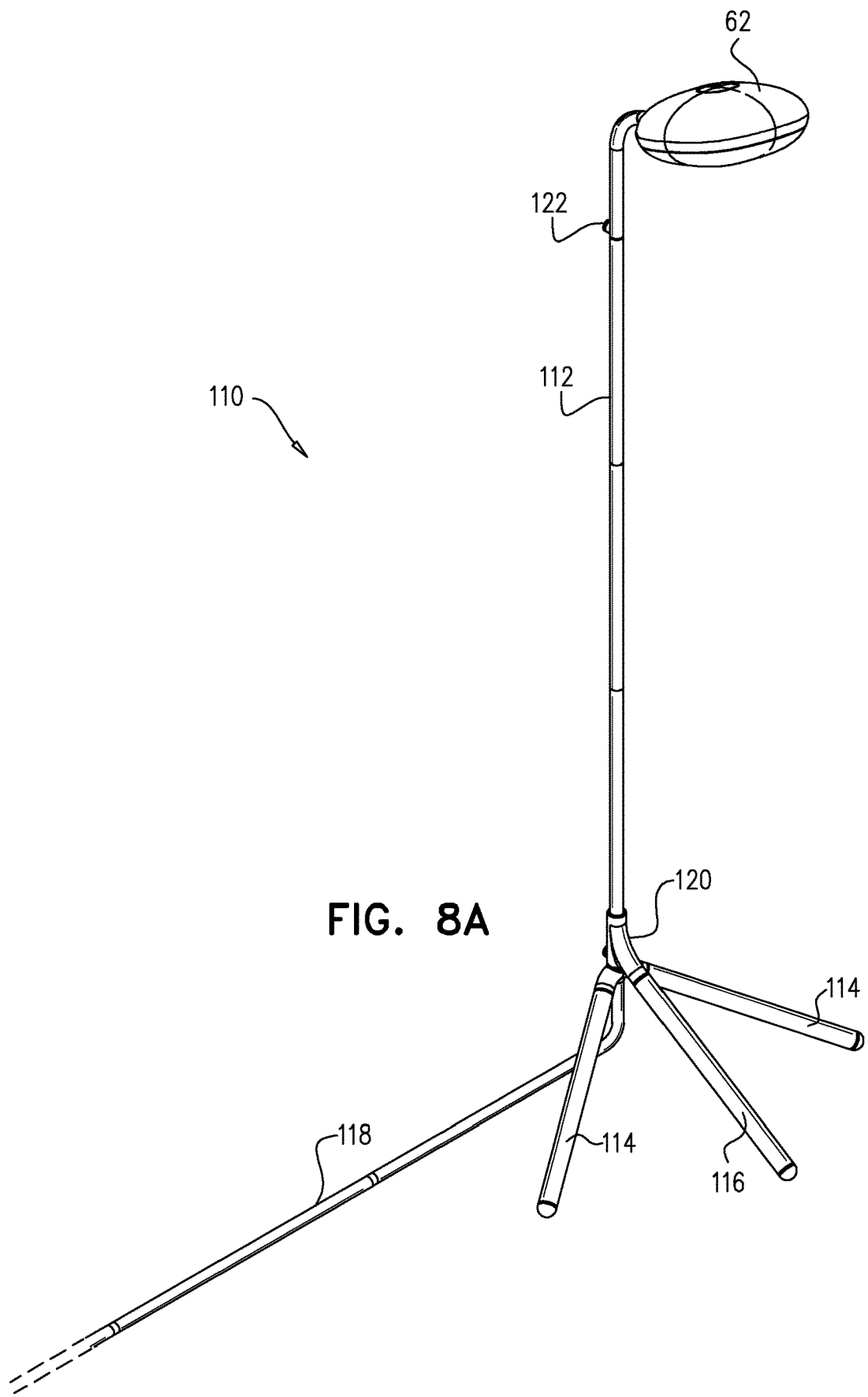
FIG. 8A is a schematic pictorial view of a sleep monitoring device with a wall-assisted floor mount, in accordance with an embodiment of the invention.

Camera head 22 is held at the end of an arm at the upper end of a tripod mount (shown in greater detail in FIGS. 7 and 8A/B). The arm is designed so that: 1) Caregiver 34 can place infant 26 in crib 24 without coming across or bumping the arm; 2) Caregiver 34 can easily reach camera head 22 to detach it from and attach it to the mount when desired; and 3) A two-year-old child will not be able to reach the mount at the point where it starts bending and thus will not be able to hang from the arm.

Camera head 22 is placed behind crib 24, at the midpoint of the long side of the crib. The natural curve of the freestanding mount achieves the optimal starting point angle (with elevation of approximately 20° above the horizontal) for the camera head. To allow flexibility in mounting position, the camera head has rotation and elevation articulation directions, as illustrated in the figures that follow. Camera head 22 is positioned and adjusted so that the camera head has a field of view 50 from a fixed perspective that encompasses the area of crib 24, along with an intervention region 52 adjacent to the crib. This perspective provides server 38 with image information that can be analyzed conveniently and reliably to detect both motions of infant 26 and actions taken by caregiver 34 in relation to the infant. Adjustment of the camera mount (as described further hereinbelow) enables the camera head angle to be changed as necessary to accommodate different mounting locations.

After assembling and setting up camera head 22 in this manner, caregiver 34 performs a simple calibration procedure: The caregiver views the video stream output by the camera head, for example on device 32 using an application dedicated to the camera, as described hereinbelow. The desired crib boundaries are overlaid as a graphical element on the image, at an offset from the center of the image chosen so that the image will also include intervention region 52. The caregiver adjusts the camera head until the actual crib boundaries match the desired boundaries shown in the overlay, and then locks the camera position. With camera head 22 locked in position, caregiver 34 clicks an "OK" control on device 32, and the camera captures an initial reference image. Subsequently, when the camera is in actual use, the captured images are registered and compared to this initial reference image in order to detect changes in the field of view. This registered image can then become the new reference image.

Monitoring Cameras

Figure 3:
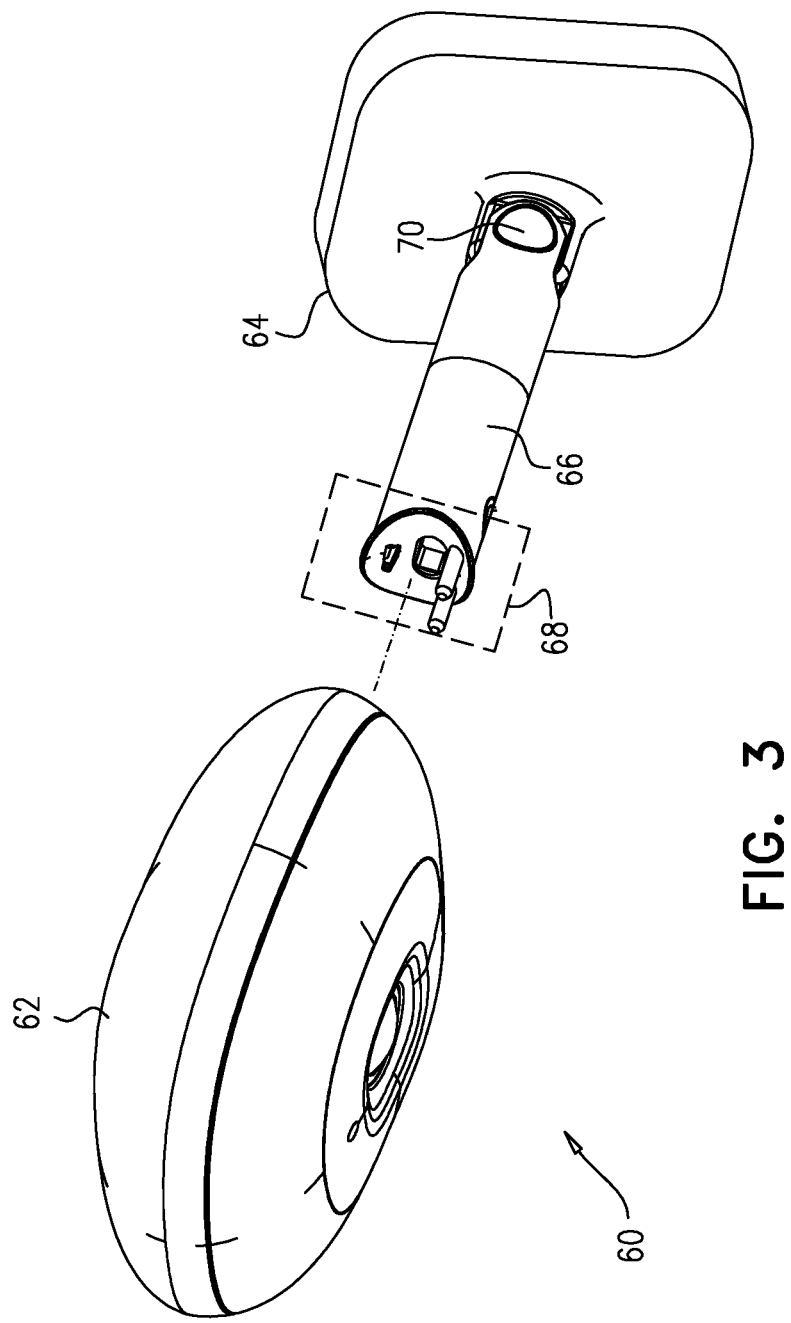
FIG. 3 is a schematic exploded view of a wall-mounted sleep monitoring device, in accordance with an embodiment of the invention.

FIG. 3 is a schematic exploded view of a wall-mounted sleep monitoring device 60, in accordance with another embodiment of the invention. In this embodiment, a monitoring camera head 62 (similar or identical in design to camera head 22 mentioned above) is held in place by a base 64, which is mounted directly on the wall, for example by a screw-in bracket. Camera head 62 is attached to base 64 by an arm 66.

A plug 68 at the end of arm 66 engages a matching socket on camera head 62 (shown in FIGS. 4A/B), which provides power to the camera head while permitting caregivers to transfer the camera head easily among different bases. Camera head 62 can be attached to various other types of mounts, as well, such as freestanding mounts (shown in the figures that follow) and mounts that attach to the crib or the ceiling. The plug on each mount has a distinguishing feature, such as a protruding pin of a different size, which fits into a receptacle on the camera head and enables the camera head to distinguish between different mounts. This information is useful in checking and updating the assumptions used in computerized analysis of the images output by the camera head.

An angle adjustment dial 70 enables the user to adjust the rotation and elevation angles of camera head 62. In some embodiments, dial 70 must to be pushed in order to change the orientation of the camera head. Consequently, when the dial is released, the viewing angle is locked, thus preventing the camera head from being moved up or down unintentionally. Alternatively, friction-based mechanisms may be used to lock the viewing angle. As noted earlier, it is helpful to keep the camera head in a fixed position to ensure that the computer vision algorithms applied by server 38 to the images of infant 26 will run accurately.

Figure 4A:
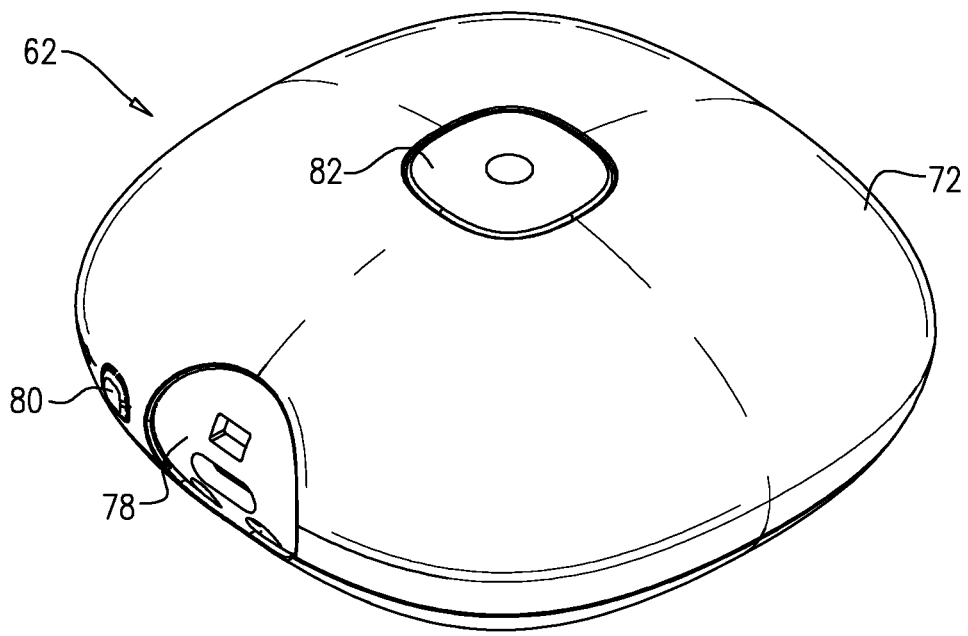
FIGS. 4A and 4B are schematic top and bottom pictorial views, respectively, of a monitoring camera head, in accordance with an embodiment of the invention.
Figure 4B:
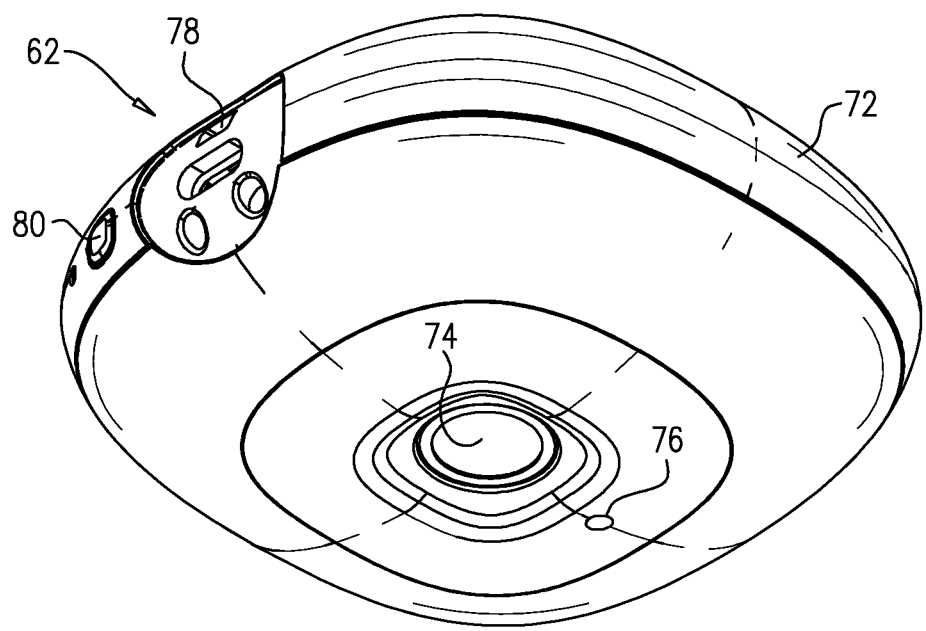
Figure 5:
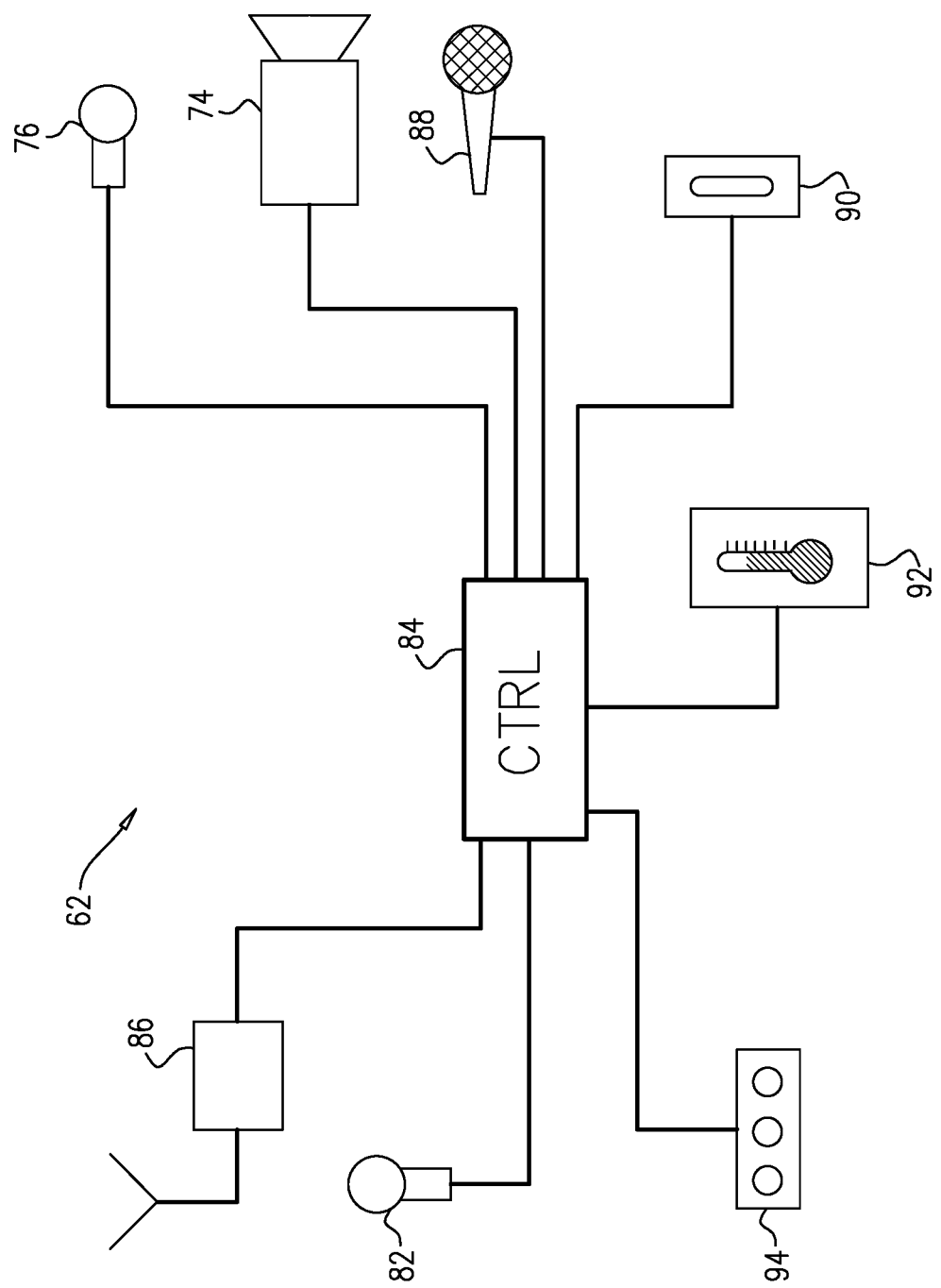
FIG. 5 is a block diagram that schematically shows functional details of a sleep monitoring device, in accordance with an embodiment of the invention.

Reference is now made to FIGS. 4A/B and 5, which schematically show details of monitoring camera head 62, in accordance with an embodiment of the invention. FIGS. 4A and 4B are schematic top and bottom pictorial views of camera head 62, respectively, while FIG. 5 is a block diagram showing functional elements of sleep monitoring device 60. Various features of device 60 are shown in the figures and described hereinbelow. Although these features can advantageously be bundled together in the manner shown here, alternative embodiments may have only one or a certain subset of these features, possibly in combination with other features and design elements that are known in the art. All such combinations are considered to be within the scope of the present invention.

The components of camera head 62 are contained inside a case 72, having a receptacle 78 for attachment to plug 68 on arm 66 (FIG. 3). An infrared (IR) light-emitting diode (LED) 76 on the lower side of case 72 illuminates the sleeping infant 26. A diffuser can be used to spread the infrared light uniformly across the crib. The diffuser is also useful in 1) reducing the red-glow effect of the IR LEDs when looking at the camera head from below; and 2) minimizing the risk of IR radiation to the child's retina. Camera head 62 comprises an infrared-sensitive image sensor 74, which may conveniently have a standard 4:3 aspect ratio to fit the size of a standard crib 24 with the addition of intervention region 52 alongside the crib. The resolution and sensitivity of sensor 74 are optimized for night conditions.

The top part of camera head 62 comprises a night light 82, which emits visible illumination. This part of case 72 is made of a semi-transparent plastic, and contains a reflector with an LED inside to support the night light effect. Night light 82 is directed toward the ceiling so that the infant at any location inside crib 24 will not see a direct light. The illumination is strong enough to enable caregiver 34 to see what is happening in the crib, but low enough to avoid waking the child. Night light 82 can be gradually dimmed on and off so that there will not be a drastic change in lighting that could wake the infant. The lighting level can be controlled by pulse-width modulation, at frequencies high enough to prevent the stimulation of an epileptic seizure in a child who may be susceptible.

Camera head 62 transmits streaming video signals over a wireless LAN (Wi-Fi) connection, using a directional antenna 86. Because the camera head is located in a known, fixed position above crib 24, the antenna is designed to minimize emission of radiation in the downward direction. Wi-Fi pairing can be performed using a Bluetooth® low-energy (BLE) link, without the need for a QR code. Pairing takes place automatically or can be invoked by pressing a Wi-Fi button 80 on camera head 62.

Camera head 62 optionally includes additional sensors and/or output devices, such as a microphone 88 and an audio speaker 90, as well as temperature and humidity sensors 92. These latter sensors can be mounted externally to case 72 (rather than inside the shell) in order to provide more accurate readings.

One or more status LEDs 94 are located in a position that is easily visible to caregiver 34, such as at the front-top side of camera head 62. For example, camera head 62 may comprise one white LED with several states, such as No light, Blinking light, and Light on. Alternatively, night light 82 can perform these signaling functions. When all is well, the light will initially be on and will then slowly (over the course of a few minutes) be turned down to avoid any unnecessary light in the room.

An internal microcontroller 84 coordinates the functions of camera head 62 under control of suitable software or firmware.

Figure 6:
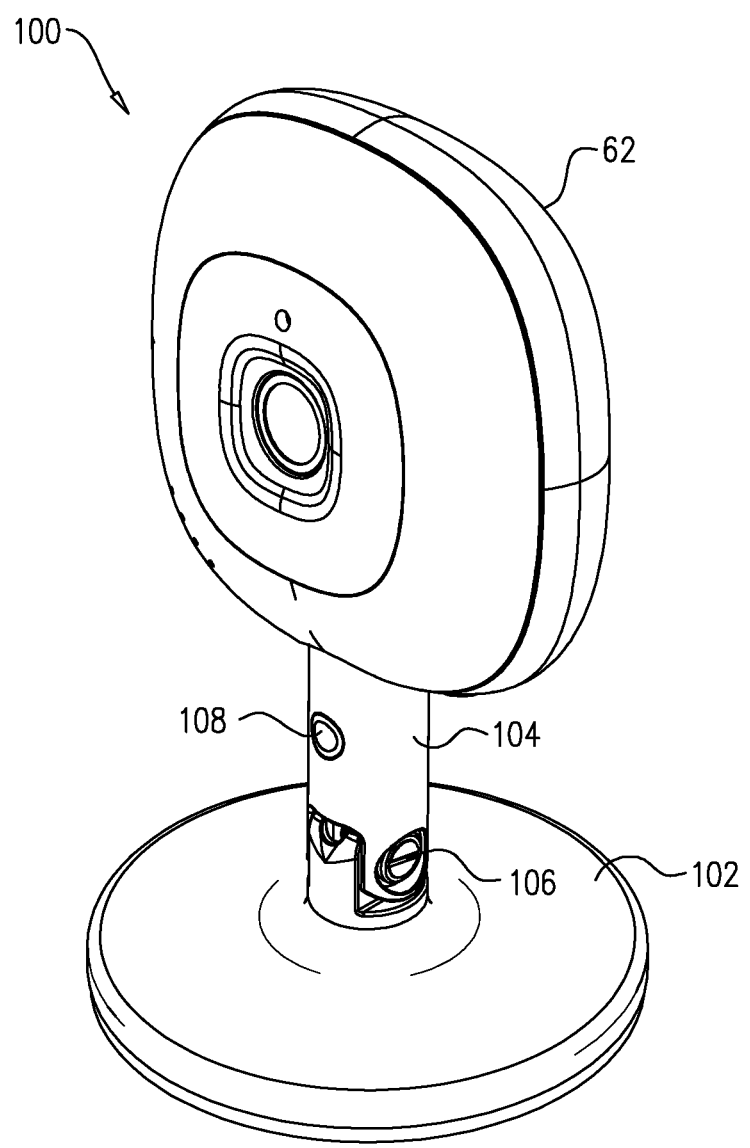
FIG. 6 is a schematic pictorial view of a table-mounted sleep monitoring device, in accordance with an embodiment of the invention.

FIG. 6 is a schematic pictorial view of a table-mounted sleep monitoring device 100, in accordance with another embodiment of the invention. Camera head 62 is the same as in the preceding embodiment, but in this case is mounted at the end of a stem 104 on a horizontal base 102, with an angle control knob or screw 106. Camera head 62 can readily be transferred by caregiver 34 from one mount to another by pressing an unlock button 108 on stem 104 with one hand while the other hand pulls the camera head away from the base. In an alternative embodiment, camera head 62 may be disconnected from stem 104 simply by pulling the camera head out of the stem, without a dedicated unlocking mechanism.

FIG. 7 is a schematic pictorial view of a freestanding sleep monitoring device 110, in accordance with an additional embodiment of the invention. Camera head 62 in this case is mounted on an arm at the top of a stem 112, with a freestanding tripod base, comprising two side legs 114 and a forward leg 116, which is held by a knuckle 120. The base shown in the figure is useful in creating a small packaging size and low overall weight of the product. The tripod can be switched to a wall-standing configuration (as shown in FIG. 2A) by rotating or removing knuckle 120, as illustrated in FIGS. 8A/B.

Camera head 62 receives electrical power from a cable (not shown), which runs through stem 112 and a rigid conduit 118 to a suitable outlet. For convenient shipping and subsequent assembly, stem 112 and conduit 118 may be broken into interlocking sections with a pre-threaded cable inside (for example, a USB cable that can support both power and, if desired, network connections). To assembly device 110, the user simply fits the sections together on site and then connects the cable to the outlet.

Figure 8B:
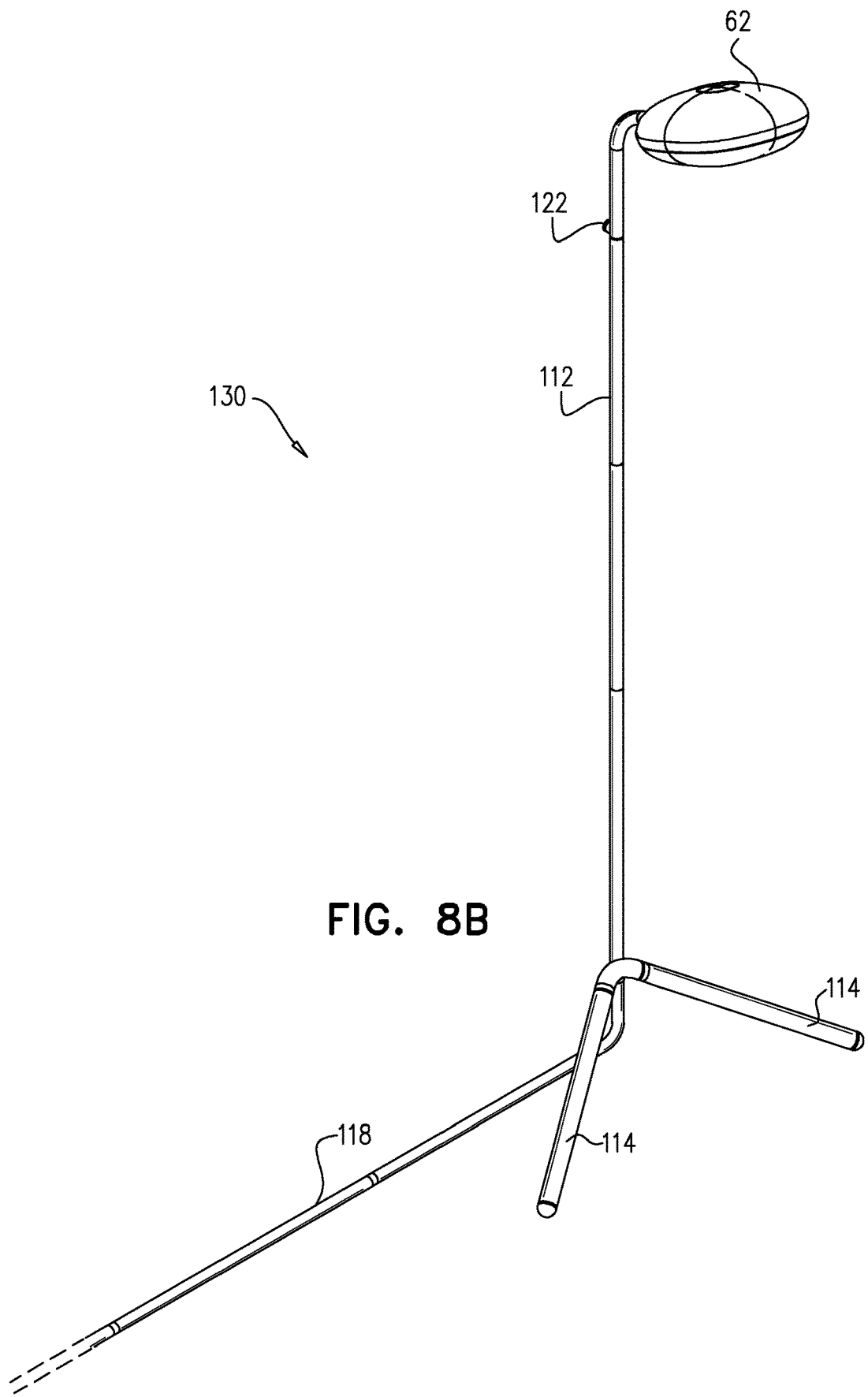
FIG. 8B is a schematic pictorial view of a sleep monitoring device with a wall-assisted floor mount, in accordance with another embodiment of the invention.

FIGS. 8A and 8B are schematic pictorial views of sleep monitoring device 110 in wall-supported floor mount configurations, in accordance with further embodiments of the invention. In these configurations, device 110 stands on the floor but is stabilized by leaning against a wall, for example as illustrated in FIG. 2A. To change from the freestanding configuration of FIG. 7 to the wall-assisted configuration of FIG. 8A, the user simply loosens knuckle 120, rotates leg 116 by 180° around stem 112, and then retightens the knuckle. Alternatively, forward leg 116 may be removed entirely, as shown in FIG. 8B. In either case, conduit 118 is turned to run along the base of the wall below crib 24.

Stem 112 includes one or more set screws 122 with a soft plastic overmold, which serve two functions: The set screws allow the rotation angle of the camera head about the base to be adjusted and locked in the proper orientation; and they act as bumpers against the wall to prevent damage to the wall and prevent movement of the base from side to side.

Figure 9:
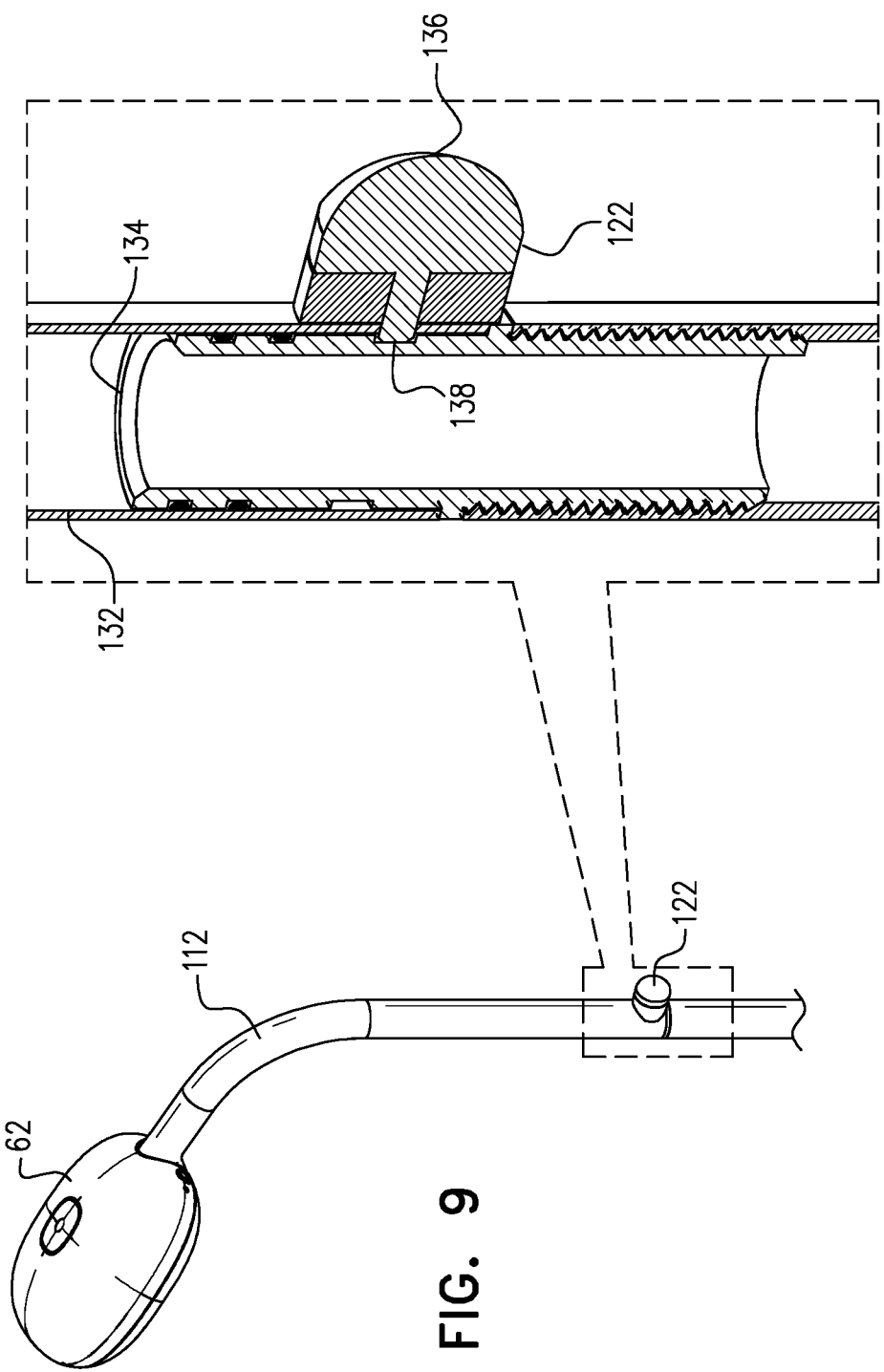
FIG. 9 is a schematic sectional view of an over-molded set screw used in a wall-assisted floor mount of a sleep monitoring device, in accordance with an embodiment of the invention.

FIG. 9 is a schematic sectional view showing details of set screw 122 on stem 112, in accordance with an embodiment of the invention. Stem 112 comprises interlocking sections 132 and 134, which can be rotated relative to one another about the stem axis. Set screw 122 can be tightened by hand so that a tip 138 of the set screw engages and locks section 134 in place relative to section 132. A soft plastic overmold 136 on set screw 122 presses against the wall behind crib 24, thus performing the bumper function mentioned above.

Caregiver Interaction

Figure 10B:
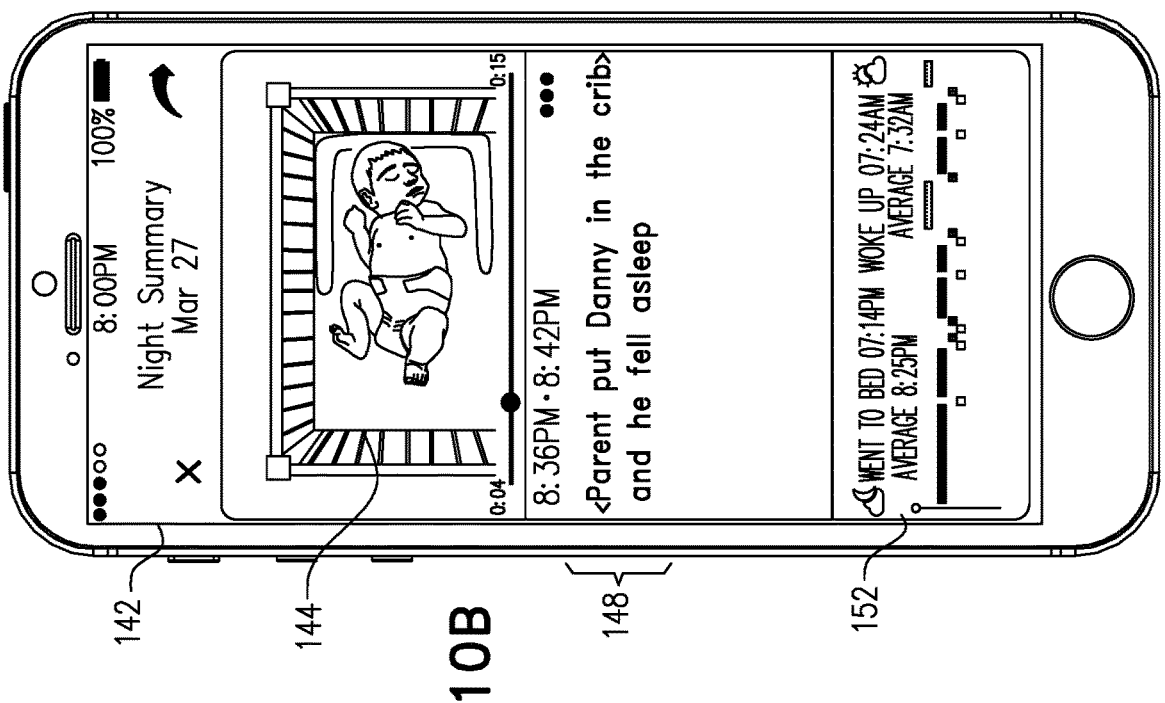
FIGS. 10A and 10B are schematic representation of user interface screens in a sleep monitoring system, in accordance with embodiments of the invention.
Figure 10A:
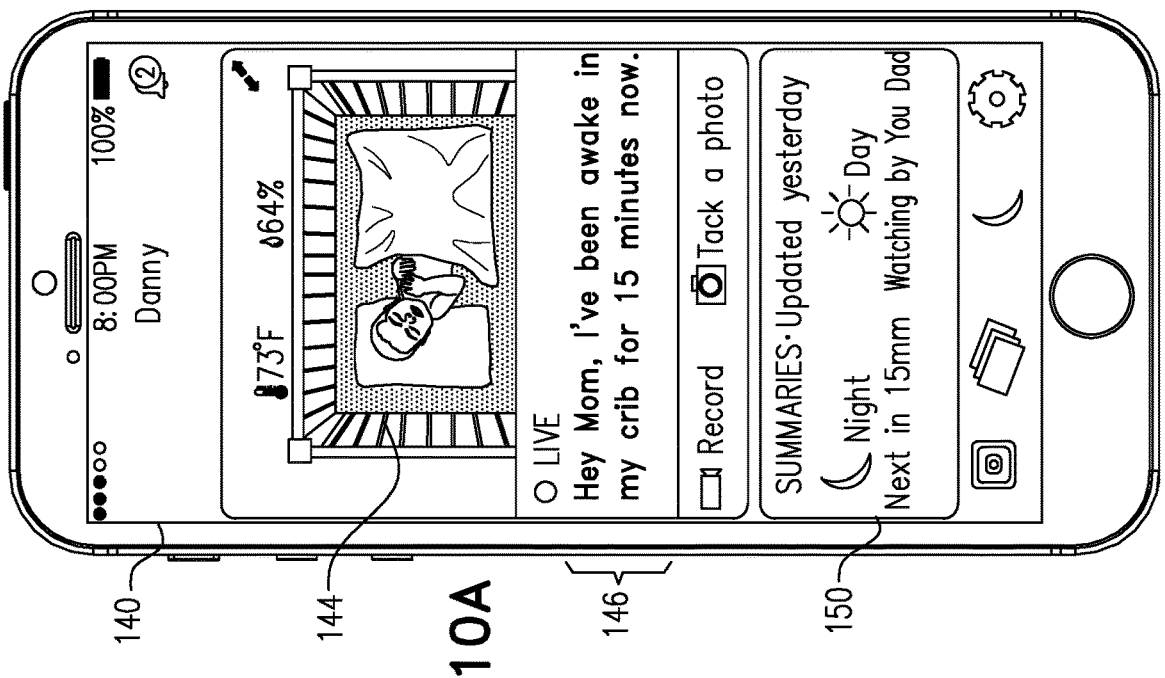

FIGS. 10A and 10B are schematic representations of user interface screens 140, 142 that are presented on client devices, such as devices 32 and 44, in sleep monitoring system 20, in accordance with embodiments of the invention. Screen 140 presents a live feed, while screen 142 presents summary information. Thus, a video area 144 in screen 140 shows live images captured by the monitoring camera mounted over the crib, along with a status message 146 and event summaries 150. On the other hand, video area 144 in screen 142 presents images of selected events that occurred during the night, as detected and logged by server 38, together with an event message 148 listing the corresponding events. A summary section 152 gives an overview of the night's sleep activity, as described further hereinbelow with reference to FIG. 11.

Server 38 detects events and generates messages 146 and 148 by processing the images captured by monitoring camera head 22. An image analysis program running on the server divides the image into two parts: inside crib 24 (I), and outside the crib (O), i.e., in intervention region 52 (FIG. 2B). Video segments with identified changes in pixels in section (I) over a series of consecutive frames are classified as Awake. Video segments with identified changes in pixels in section (O) along a series of consecutive frames are classified as Visit. Segments between Awake-Awake, Visit-Awake, and Awake-Visit are classified as Asleep, while other segments are classified as Away, meaning that the infant is not in the crib.

Furthermore, the Visit state can be divided into sub-states depending on the nature of the caregiver interaction, for example: check-in, taking care, and removing the infant from of or placing the infant in the crib. To distinguish between these states, server analyzes movement occurring both in the crib and in the intervention region. If the infant is in the crib and movement is detected outside the crib, the visit sub-state is classified as "check-in." If the infant is in the crib and movement occurs both outside and inside the crib, the visit sub-state is classified as "taking care." If the infant is in the crib, movement is detected outside of the crib, and then subsequently there is no infant in the crib, then the visit sub-state is "removal of infant," and vice versa for "placement of infant" in the crib.

Table I below presents example events, based on changes in the states of the images analyzed by server 38, along with the messages to the caregiver that are generated in response to each event. As noted earlier, these events relate to the behavior of both the infant and caregivers, and thus can assist caregivers in modifying their own behavior in a way that will encourage good sleep habits by the infant. Status message 146 typically lists the most recent event, along with the time elapsed since its occurrence, while event message 148 lists events that occurred in the course of the night.

TABLE I

BEHAVIORAL EVENTS AND MESSAGES

| Transition | Scenario in the video | Messaging |
| --- | --- | --- |
| Away -> Visit -> Asleep | Caregiver is putting baby in bed asleep | Danny was put to bed already sleeping |
| Away -> Visit -> Awake -> Asleep | Caregiver is putting baby in bed awake and baby falls asleep by himself after less than 2 minutes | Danny was put to bed awake and quickly fell asleep without help. |
| Away -> Visit -> Awake | Caregiver is putting baby in bed awake | Danny was put to bed awake |
| Awake -> Asleep | Baby falls asleep by himself after X minutes (more than 2 min) | Danny fell asleep without help after X minutes. Sleep success! |
| Asleep -> Awake -> Asleep | Baby wakes up after sleeping for Y hours and falls asleep in X minutes (less than 10 min) | Danny woke up briefly after sleeping Y hours, then fell back to sleep without any help in X minutes. |
| Asleep -> Awake | Baby wakes up after sleeping for Y hours | Danny slept Y hours and then woke up for a bit |
| Awake -> Asleep | Baby falls asleep in X minutes (more than 10) | Danny fell back to sleep without any help after X minutes. |
| Asleep -> Awake -> Visit | Caregiver intervenes less than 5 minutes after baby wakes up | Danny woke up and was taken care of right away |
| Asleep -> Awake | Baby wakes up | Danny woke up after sleeping Y hours |
| Awake -> Visit | Caregiver intervenes more than 5 minutes after baby wakes up | Someone checked up on and took care of Danny |
| Asleep -> Awake -> Visit -> Away | Caregiver removes the baby from crib less than 5 minutes after the baby wakes up | Danny slept for Y hours, woke up and then was taken out of the crib |
| Asleep -> Awake | Baby wakes up | Danny woke up after sleeping for Y hours |
| Awake -> Visit -> Away | Caregiver removes the baby from crib more than 5 minutes later | Danny was taken out of the crib |
| Asleep -> Visit -> Away | Caregiver removes the sleeping baby from crib | Danny was taken out of the crib while still sleeping |
| Asleep -> Visit -> Asleep | Caregiver approaches the crib, does something (e.g., covers the baby with a blanket or puts in pacifier), then goes away | Someone quickly checked up on Danny -- everything looked good! |

TABLE I-continued

BEHAVIORAL EVENTS AND MESSAGES

| Transition | Scenario in the video | Messaging |
|---|---|---|
| Asleep –> Visit | * If the visit is long | Someone checked up on Danny |
| Visit –> Asleep | | Danny was left alone to get some zzz's. |

The content in the messaging column above is described by way of example, and other implementations are also considered to be within the scope of current invention. For instance, "Someone checked up on Danny" can be switched with "Danny had a visitor" or "Caregiver visited Danny," etc.

Figure 11:
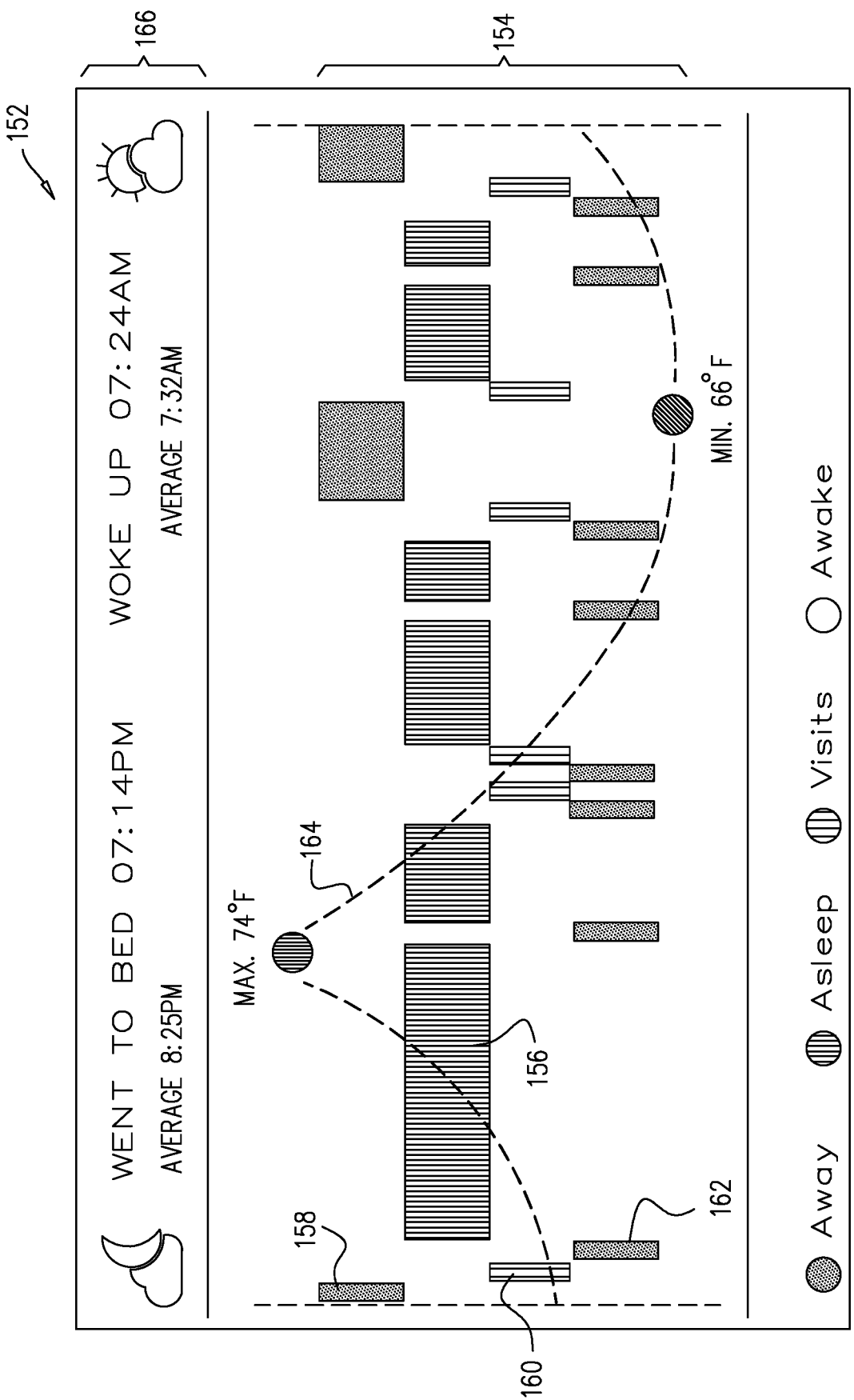
FIG. 11 is a summary plot of nighttime activity presented by a sleep monitoring system, in accordance with an embodiment of the invention.

FIG. 11 shows details of summary section 152 of nighttime activity presented on screen 142, in accordance with an embodiment of the invention. Section 152 includes a time plot 154, which displays caregiver presence in the scene of the crib and correlates it with infant sleep and wake periods, temperature and humidity. The plot also displays periods in which the infant was not in the crib. Specifically, plot 154 is made up of bars 156 showing periods during which the infant was asleep in the crib, bars 158 indicating the periods during which the infant was out of the crib, bars 160 indicating caregiver visits, and bars 162 indicating periods during which the infant was awake in the crib. Plot 154 thus enables caregivers to visualize the entire pattern of their interactions with the infant and its effect on infant sleep and waking periods.

Section 152 also provides other summary information, including a plot 164 of temperature (as measured by sensor 92) and sleep and waking time data 166 computed by server 38.

Server 38 may analyze and present, on screen 142, separate video summaries of nighttime and daytime activities. These summaries include time-lapse video clips in window 144, along with corresponding event messages 148, as described above. The night summary can use sleep analytics to generate a sleep quality score, based on criteria such as time to sleep onset, total time asleep, sleep efficiency (total time asleep divided by total time in bed), and number and duration of visits by caregivers. Furthermore, server 38 can distinguish between and report different type of visits, such as check-in, taking care, and taking the baby out of or into the crib. The day summary is an aggregation of naps that occurred in the period of the day and typically includes the total time asleep and the last time asleep and wakeup time (which help to plan the next nap), as well as details such as the number of naps and total time in bed.

The night and the day summaries are separated by the "night_start" and "night_end" points of each day. The night_start is typically set to be the last time the infant is put in the crib before the night's sleep and after 6 PM. (This time is a default, which caregivers can modify, taking into account the normal day routine in Western countries.) The night_end is the first time the infant is taken out of the crib after the night sleep and before 9 AM (again, a default that can be modified). The period between night_start and night_end is the range for collecting the events for the night summary, while the period between night_end and the next night_start is the range for collecting the events for the day summary, with similar logic to that described above. The summaries can be made available to caregivers via event summaries 150 on screen 140, for example.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A video monitoring system, comprising:
a camera head, comprising an infrared illumination source and an image sensor and is configured to transmit streaming video signals generated by the image sensor;
a mount, which is configured to hold the camera head in a fixed location and orientation above a bed such that the image sensor captures images from a bird's eye view of a child in the bed with a field of view from a fixed perspective that encompasses the area of the bed; and
a processor, which is configured to receive and analyze the video signals so as to extract and provide information to a client device with regard to a behavior of the child,
wherein the mount is selected from a set of mounts including a base having multiple legs for floor mounting and a flat base for at least one of shelf mounting and wall mounting, and the camera head is configured to be attached to and detached from any of the mounts in the set.

2. The system according to claim 1, wherein the processor is configured to extract and provide the information with regard to sleep behavior of the child.

3. The system according to claim 1, wherein the processor is configured to extract and provide the information with regard to development milestones of the child.

4. The system according to claim 1, wherein the mount is configured so that the image sensor captures images of the bed and an intervention region adjacent to the bed.

5. The system according to claim 1, wherein the camera head comprises a receptacle configured to accept a plug on the mount, and wherein the plug on each of the mounts has a distinguishing feature that fits into the receptacle and enables the camera head to identify the mount to which the camera head is attached.

6. The system according to claim 1, wherein the infrared illumination source directs infrared illumination toward the crib from a lower side of the camera head.

7. The system according to claim 1, wherein the camera head is configured to transmit the streaming video signals over a local network in data packets that are addressed so that the video signals are forwarded both locally to the client device on the local network and via a public network to a remote server, from which video images are available remotely to the client device.

8. The system according to claim 1, wherein the camera head is configured to transmit the streaming video signals over a network to a server, which comprises the processor, and the server is configured to analyze the video signals so as to extract and provide the information regarding the behavior of the child.

9. The apparatus according to claim 1, wherein the processor is configured to analyze the streaming video signals so as to detect and log events associated with the behavior of the child.

10. The apparatus according to claim 9, wherein the processor is configured to output a summary of the logged events to the client device.

11. The apparatus according to claim 10, wherein the processor is configured to present the summary in a graphical form, which indicates states of behavior of the child and respective periods of time during which the states occurred.

12. A video monitoring system, comprising:
a camera head, comprising an infrared illumination source and an image sensor and is configured to transmit streaming video signals generated by the image sensor;
a mount, which is configured to hold the camera head in a fixed location and orientation above a bed such that the image sensor captures images from a bird's eye view of a child in the bed with a field of view from a fixed perspective that encompasses the area of the bed; and
a processor, which is configured to receive and analyze the video signals so as to extract and provide information to a client device with regard to a behavior of the child,
wherein the infrared illumination source directs infrared illumination toward the crib from a lower side of the camera head, and
wherein the camera head comprises a night light, which is configured to emit visible illumination from an upper side of the camera head.

13. A video monitoring system, comprising:
a camera head, comprising an infrared illumination source and an image sensor and is configured to transmit streaming video signals generated by the image sensor;
a mount, which is configured to hold the camera head in a fixed location and orientation above a bed such that the image sensor captures images from a bird's eye view of a child in the bed with a field of view from a fixed perspective that encompasses the area of the bed; and
a processor, which is configured to receive and analyze the video signals so as to extract and provide information to a client device with regard to a behavior of the child,
wherein the processor is configured to analyze the streaming video signals so as to detect and log events associated with the behavior of the child,
wherein the images include an intervention region adjacent to the bed, and wherein at least some of the events that are detected and logged by the processor are based on analyzing actions of a caregiver in the intervention region.

14. The system according to claim 13, wherein the mount comprises a tripod base comprising three legs, wherein one of the legs is rotatable or removable in order to transform the mount from a freestanding configuration to a wall-supported configuration.

15. The system according to claim 14, wherein the mount is configured to stand between the crib and a wall adjacent to the crib and comprises at least one overmolded set screw, which is configured both to enable rotation and locking of the mount and to serve as a bumper against the wall.

16. A method for monitoring, comprising:
providing a camera head, comprising an infrared illumination source and an image sensor;
providing a mount configured to hold the camera head in a fixed location and orientation above a bed with a field of view from a fixed perspective that encompasses the area of the bed such that the image sensor captures images from a bird's eye view of a child in the bed; and
receiving and analyzing streaming video signals generated by the image sensor so as to extract and provide information to a client device with regard to a behavior of the child,
wherein analyzing the streaming video signals comprises extracting and providing the information with regard to development milestones of the child.

17. The method according to claim 16, wherein analyzing the streaming video signals comprises extracting and providing the information with regard to sleep behavior of the child.

18. The method according to claim 16, wherein the mount is configured so that the image sensor captures images of the bed and an intervention region adjacent to the bed.

* * * * *